(12) United States Patent
Eckermann

(10) Patent No.: US 8,475,419 B2
(45) Date of Patent: Jul. 2, 2013

(54) AUTOMATED BODY FLUID DRAIN CONTROL APPARATUS AND METHOD

(75) Inventor: Jan Eckermann, Los Angeles, CA (US)

(73) Assignee: Beckersmith Medical, Inc., Los Angeles, CA (US)

( * ) Notice: Subject to any disclaimer, the term of this patent is extended or adjusted under 35 U.S.C. 154(b) by 784 days.

(21) Appl. No.: 12/197,201

(22) Filed: Aug. 22, 2008

(65) Prior Publication Data

US 2009/0054857 A1    Feb. 26, 2009

Related U.S. Application Data

(60) Provisional application No. 60/966,132, filed on Aug. 25, 2007.

(51) Int. Cl.
*A61M 1/00*    (2006.01)

(52) U.S. Cl.
USPC ........... 604/318; 604/187; 604/192; 604/268; 604/289; 604/290; 604/296; 604/300; 604/304; 604/311; 604/312; 604/315; 604/316; 604/35; 604/36

(58) Field of Classification Search
USPC .................... 604/313, 315, 316, 318
See application file for complete search history.

(56) References Cited

U.S. PATENT DOCUMENTS

| 5,207,661 | A  | 5/1993 | Repschlager |
| 5,656,027 | A  | 8/1997 | Ellingboe |
| 5,741,238 | A  | 4/1998 | Bradbury |
| 6,336,924 | B1 | 1/2002 | Lecuyer |

FOREIGN PATENT DOCUMENTS

WO    WO2005035025 A1    4/2005

OTHER PUBLICATIONS

Written Opinion of the International Searching Authority and International Search Report with a mailing date of Nov. 3, 2008, issued in related application PCT/US2008/074125.
Supplemental Search Report issued on May 23, 2012 in related EPO application 08828696.8.

*Primary Examiner* — Tatyana Zalukaeva
*Assistant Examiner* — Ilya Treyger
(74) *Attorney, Agent, or Firm* — Jeffer Mangels Butler & Mitchell LLP

(57) ABSTRACT

Described herein is an automated fluid drain control apparatus and method which comprises a first collection chamber which is connected to a drain that has been inserted into the subarachnoid area in lumbar region of the body. The volume of fluid into the first collection chamber is controlled as a function of time by being constantly measured such that too much fluid will not be drained from the body.

20 Claims, 2 Drawing Sheets

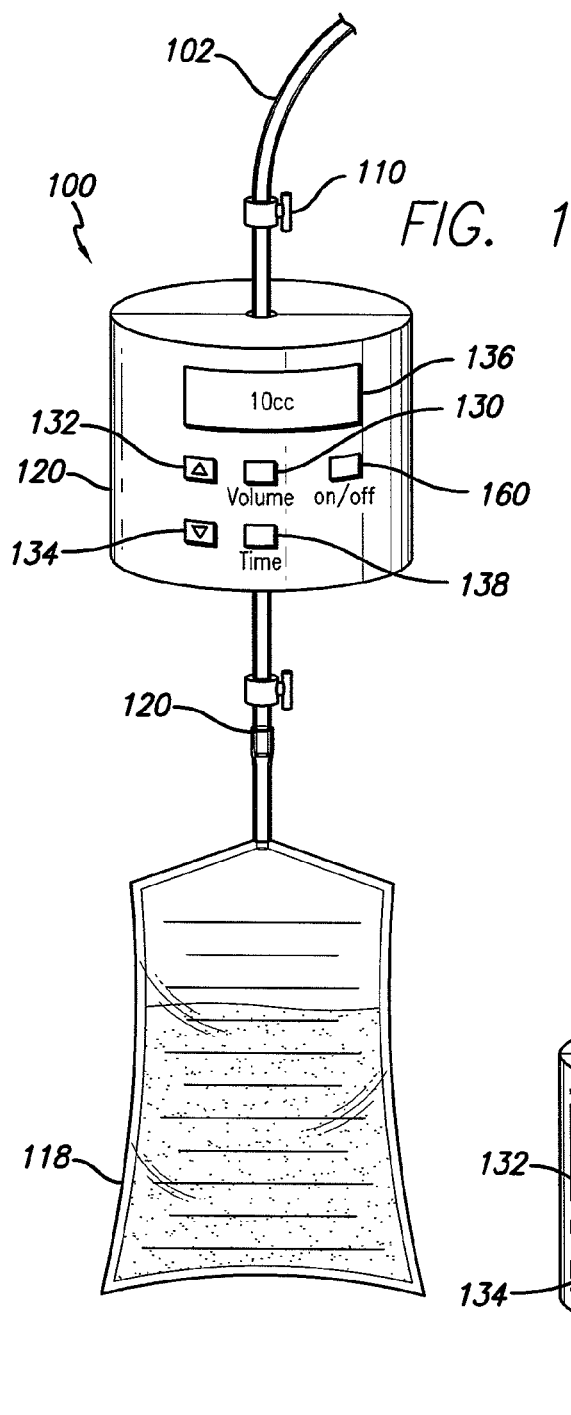

01:20
AUTOMATED BODY FLUID DRAIN CONTROL APPARATUS AND METHOD

This application claims the benefit of U.S. Provisional Application No. 60/966,132 filed Aug. 25, 2007, which is herein incorporated by reference in its entirety.

FIELD OF THE INVENTION

The present invention relates generally to fluid collection devices from the body. More specifically, this invention relates to cerebrospinal fluid drainage and collection devices and methods for controlling the drainage.

BACKGROUND OF THE INVENTION

Body fluid drains and containers are well known in the art. For example, there are collection devices for urine and others that drain and collect spinal fluid. None of these devices are able to easily control the drainage rate of the fluid as a function of time.

In connection with the drainage of cerebrospinal fluid ("CSF"), for most people, the body produces 450 ccs of CSF over a 24 hour period which fills the subarachnoid space in the body. There are many instances where it may be advisable and/or necessary for some of the CSF to be drained. For example, during certain medical procedures such as brain surgery, the surgeon may wish to drain some of the CSF in order to retract the brain. In addition, in some brain and spinal surgeries where the dura mater is penetrated, the CSF would need to be partially drained to keep pressure off the wound site in order to allow it to heal. Also, in certain head trauma cases where CSF is collecting in the cranial cavity, it may be preferable to drain some of the CSF from the subarachnoid space in the lumbar spinal region to relieve the pressure on the brain.

Conventional methods of draining CSF involve tapping into the cranial or subarachnoid space in the spinal column and draining the excess CSF through a catheter tube into a collection bag. The amount of drainage must be regulated, as if there is too much drainage, a patient can be irreversibly injured or can be fatally injured.

Unfortunately, the rate at which the CSF drains is not linear fashion. For example, the CSF can drain at 1 cc per hour and then suddenly drain 5 ccs in 10 minutes. Since there are irreversible and potentially fatal consequences if too much CSF is drained, the volume of the drainage has to be constantly monitored by a nurse. Due to the demand on a nurse's time and the non-linearity of the drainage, there is a potentially fatal margin of error. Thus, an apparatus that continuously monitors and controls the drainage of the CSF would be of great benefit to the art.

SUMMARY OF THE PREFERRED EMBODIMENT AND METHOD

In a preferred embodiment of the present invention, an automated fluid collection apparatus comprises a first tube having a first end connected to a drain that has been inserted into a patient's subarachnoid region and a second end connected to an opening at the proximal end of a first collection chamber. The first collection chamber also has an opening at the distal end thereof. In one embodiment the chamber has a first valve or first controllable closing mechanism proximate the opening at the proximal end and a second valve or controllable closing mechanism at the distal opening thereof. In another embodiment, there is a second tube having a first end and a second end, whereby the first end is connected to the opening at the distal end of the collection chamber. In the preferred embodiments of the present invention, the first and second valves may be located on the first and second tubes respectively or on the proximal and distal ends of the first chamber. In one preferred embodiment, the distal end is connected directly to a collection bag; in another embodiment the second tube is connected at the second end to a second collection chamber or bag.

In the preferred embodiment, the apparatus also comprises a measuring device which determines the amount of fluid that is being collected in the first chamber over a preselected period of time. In one preferred embodiment, the measuring device is an optical sensor connected to a spectrophotometer which is able to detect specific wavelengths inside the chamber so as to determine the amount of fluid collected herein. In other alternate embodiments, a different type of fluid measuring device may be used. In an alternate embodiment, the measuring device may also be able to sense the type of fluid collected in the chamber to detect any anomalies therein.

The apparatus also comprises a timer, microprocessor and power supply which are connected to the measuring device and to the controllable closing mechanisms so that the amount of fluid collected in the first collection chamber is constantly being measured, monitored and controlled. The microprocessor processes the various measurements received from the measuring device to determine the volume contained within the first chamber. The timer controls the period of time over which the fluid is measured and collected within the first chamber and is reset for each new period of time as instructed by the processor. Once the microprocessor determines that the first chamber is filled to a preselected level at any time prior to the expiration of the selected time period, it will cause the first valve to close and the second valve to open such that the first chamber will be emptied and so that the drainage will discontinue for the remainder of the preselected time period. In this manner, the drainage rate of the fluid will never be more than the preselected level during the preselected period of time.

In the preferred method of the present invention, the first end of the first tube is attached to a drain that has been inserted into the appropriate subarachnoid region of the body. The first valve is opened and the second valve is closed. The timer is also set for either a default or an alternate timer period as is the maximum volume for the first chamber.

Thereafter, the CSF fluid drains through the proximal valve into the first collection chamber through the use of gravity. As the fluid drains into the first chamber, the volume of the first chamber is constantly measured by the measuring device. Once the microprocessor determines that the first chamber is filled to a preselected level at any time prior to the expiration of the then applicable preselected time period, it will cause the first valve to close and the second valve to open such that the first chamber will be emptied and so that the drainage will discontinue for the remainder of the preselected time period. In this manner, the drainage rate of the fluid will never be more than the preselected level during the preselected period of time. At the end of each preselected time period the timer will reset.

If the first chamber has not attained the maximum preselected volume in the preselected time period, the first valve will remain open and the second valve will remain closed and the drainage will continue until the maximum volume is attained.

If at any time there is any problem with the system or if the first collection chamber fails to fully empty at each predetermined interval, an alarm will notify the appropriate personnel that their attention is required.

BRIEF DESCRIPTION OF THE DRAWINGS

The invention may be more readily understood by referring to the accompanying drawings in which:

FIG. 1 is a perspective view of a preferred embodiment of the apparatus of the present invention in a closed position.

FIG. 2 is a partial view of an alternate e embodiment of the apparatus of the invention in a closed position.

Like numerals refer to like parts throughout the several views of the drawings.

DETAILED DESCRIPTION OF THE PREFERRED EMBODIMENTS

Figure 3:
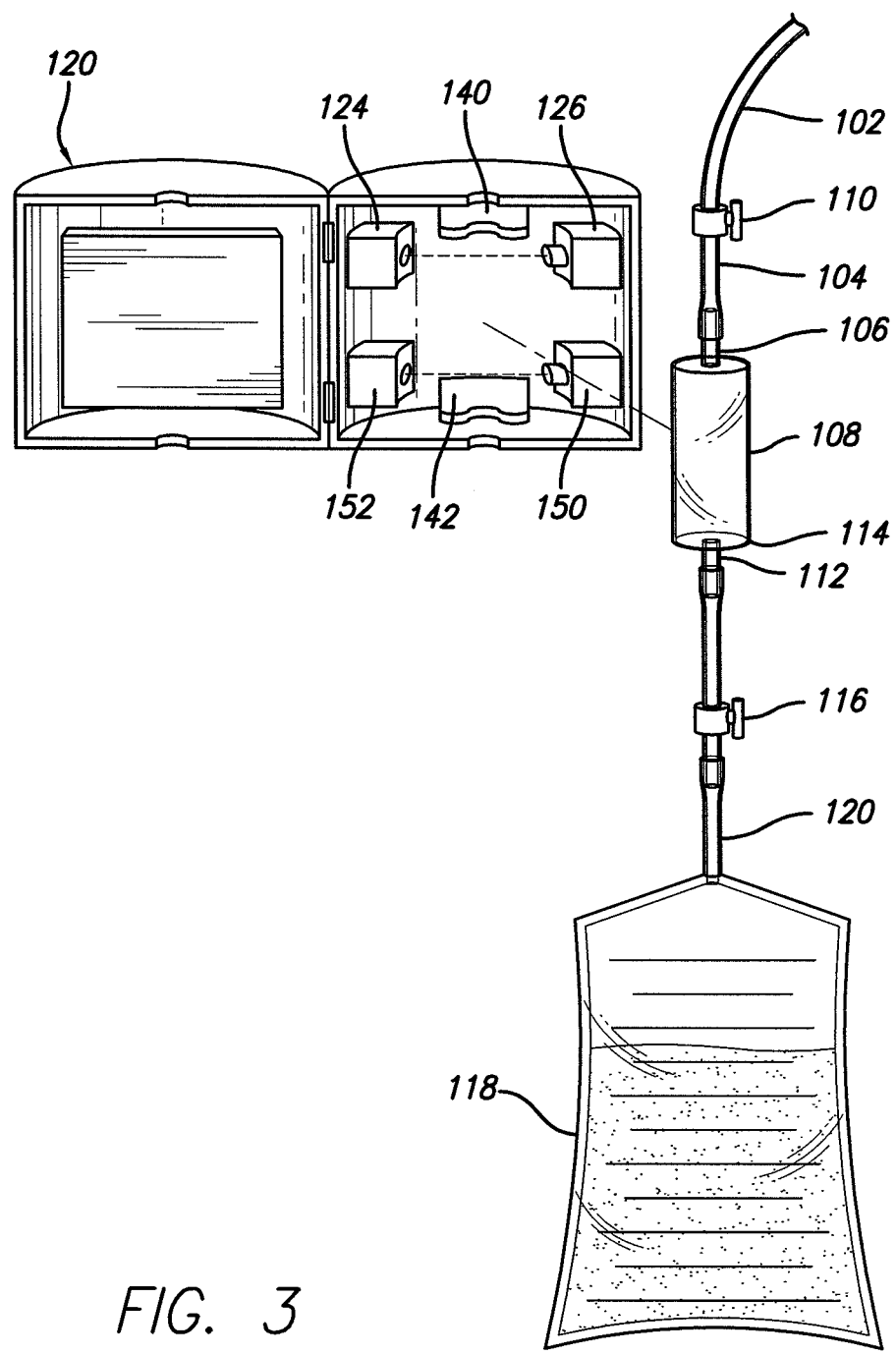
FIG. 3 is an exploded view of the preferred embodiment of FIG. 1 in an open position.

In the following descriptions of the invention, terms such as "front," "back," "top," "bottom," "side," and the like are used herein merely for ease of description and refer to the orientation of the components as shown in the Figures.

Generally, the present invention may be briefly described as follows. Referring first to FIGS. 1 and 2, a preferred embodiment of an automated fluid drain control apparatus 100 of the present invention is shown.

The automated fluid drain control apparatus 100 comprises a comprises a first tube 102 having a first end (not shown) connected to a drain (not shown) that has been inserted into a patient's subarachnoid region and a second end 104 connected to an opening 106 at the proximal end of a first collection chamber 108. In a preferred embodiment, the first collection chamber 108 has a first valve 110 or other suitable first controllable closing mechanism known in the art that is capable of opening and closing the flow of fluid between first tube 102 and the first collection chamber 108. In the preferred embodiments shown in FIGS. 1, 2 and 3, valve 110 is located on tube 102. However, in an alternate embodiment, not shown, there is no valve 110. In the embodiment shown, valve 110 is a manual valve that can be opened and closed by the user of the apparatus. However, in alternate embodiments, the valve 110 can be controlled electronically.

The first collection chamber 108 also has an opening 112 at the distal end 114 thereof. In FIG. 2, an alternate embodiment is shown in which the first collection chamber 108 has a second valve 116 or other suitable second controllable closing mechanism known in the art that is capable of opening and closing the flow of fluid out of the distal end 114 of the first collection chamber 108. In the embodiments shown in FIG. 1 and 3, there is a second collection chamber 118 with a neck 120 which is connected to the opening 112 at the distal end 114 of the first collection chamber 108. In yet another embodiment (not shown) a second tube having a first end and a second end is connected at the first end to the opening 112 at the distal end 114 of the collection chamber 108. In that embodiment, the second tube is also connected at the second end to a second collection chamber or bag such as the one shown in FIGS. 1 and 3.

In a preferred embodiment, the apparatus 100 also includes a housing 120 which houses the first chamber 108 and the electronics (not shown) which include a microprocessor (not shown), a timer (not shown), a power supply (not shown) and relays (not shown) which control third and fourth valves 140 and 142. The third 140 and fourth 142 valves are either pinch valves or any other mechanism known in the art that are controllable and which can easily and quickly impede the flow of fluid. In addition, in a preferred embodiment shown in FIG. 3, the third and fourth valves 140 and 142 are located in the housing proximate the beginning of the first and second tubes so that they can impede the flow of fluid into and out of the first collection chamber 108. However, in alternate embodiments there is only one set of valves such that either valves 102 and 116 are controlled electronically such that there is no need for third and fourth valves or valves 102 and 116 are unnecessary. However, in order to provide a fail safe mechanism, in the preferred embodiment, all four valves are used.

In addition, the housing 120 also contains a first measuring device connected to the microprocessor which together determine the amount of fluid that is being collected in the first chamber 108 over a preselected period of time. In one preferred embodiment, shown in FIG. 3 the measuring device is an optical sensor 124 connected to a spectrophotometer 126 which is able to detect specific wavelengths by shining a light through the first collection chamber 108 so as to determine the amount of fluid collected therein. In other alternate embodiments, a different type of fluid measuring device may be used with suitable modifications to the electronics and microprocessor. By way of example, and not limitation, such measuring devices may include, a weight measuring device that measures the amount of fluid collected within the first collection chamber 108 based upon weight; an acoustic sensor coupled with a sound generator which sends sound waves through the chamber 108 in order to detect the amount of fluid based upon the change in the sound waves as they traverse the fluid; a capacitive sensor either located within the first collection chamber to measure a variable such, as, but not limited to, the pressure inside the chamber created by the changes in the volume of fluid to determine the volume or depending on the material of the chamber, detect and measure deformations of the chamber again to determine volume; a flowmeter; a thermo sensor; a ph sensor; a device that uses the technology of microfluidics; or any other fluid measuring device known in the art.

In various embodiments of the present invention with suitable additional software added to the microprocessor, the measuring device also is able to detect any anomalies such as, but not limited to, the presence of blood, white cells, pus, dye, etc.

The microprocessor is connected to the measuring device, the timer and the relays. In the embodiment shown in FIGS. 1-3, the relays are connected to the third and fourth valves 140 and 142. However, in an alternate embodiment in which there are no third and fourth valves, the relays are connected to the first and second valves 110 and 116.

The microprocessor ensures that the fluid inside the first collection chamber constantly is being measured, monitored and controlled. The microprocessor also processes the various measurements received from the measuring device to determine the volume contained within the first chamber.

In one embodiment, the user can select the maximum volume that can be collected in the first collection chamber 108 during a selected period of time. In the embodiment shown in FIGS. 1 and 2, that is accomplished by pressing the volume control button 130 located on the front of housing 120 and thereafter pressing up and down indicator buttons 132 and 134 which sends a signal to the microprocessor which then stores the amount of maximum volume selected in its memory. Alternate selections means well known in the art can be used in lieu of the buttons shown in FIGS. 1 and 2. In addition, in embodiments such as is shown in FIGS. 1 and 2, an visual display 134 is shown on the front of the housing 120 which shows the volume amount selected.

In another embodiment, the microprocessor selects the default value for the amount of volume that can be selected during a selected period of time. Regardless of how the volume is selected, the volume value regulates how many times the chamber will empty per preselected time period.

In another embodiment, the user can select the period of time over which the fluid is measured and collected within the first chamber. In the embodiment shown in FIGS. 1 and 2, that is accomplished by pressing the timer control button 138 located on the front of housing 120 and then up and down indicator buttons 132 and 134 which sends a signal to the microprocessor which then stores the amount of time selected in its memory. In addition, in an embodiment such as is shown in FIG. 1, the visual display 136 is shown on the front of the housing 120 which shows the timer amount selected. This also will regulate how many times the chamber will empty per preselected time period. If the timer is not manually set by the user, then the timer will set a default for the preselected time period. In another embodiment, which does not have a manual controller, the timer may be preselected by the microprocessor. In yet a further embodiment, the apparatus provides either means of selecting the period of time.

Regardless of the embodiment used, once the microprocessor determines that the first chamber is filled to a preselected level at any time prior to the expiration of the then applicable preselected time period, it will cause the appropriate valve to close which in the preferred embodiment shown in FIG. 3 is third valve 140 and the appropriate other valve to open which in the preferred embodiment shown in FIG. 3 is the fourth valve 142. In alternative embodiments in which only valves 110 and 116 are being used, then the microprocessor will cause first valve 110 to close and second valve 116 to open. In this manner, the first collection chamber 108 will be emptied and drainage will discontinue for the remainder of the preselected time period. As a result, the drainage rate of the fluid will never be more than the preselected level during the preselected period of time.

In addition, in various embodiments, the microprocessor also can determine and display the total volume drained over a larger time period on display 136 by holding down the volume button for a preselected period of time, although other embodiments may use other techniques well known in the art for obtaining the information with suitable modifications of the electronics.

In addition, to the foregoing, the apparatus may also contain an additional spectrophotometer 150 and related sensor 152 to assure the complete emptying of the first collection chamber at the end of each appropriate cycle. In addition, the apparatus may also contain an alarm producing mechanism (not shown) whereby if the information sent by the measuring device as processed by the microprocessor detects that blood or other types of fluid or cells are present in the fluid, the nursing staff will be alerted. Likewise, with suitable additional electronics, other alerts may be present such as when there is a kink in the tubing, the power fails, or one of the components of the system is not operating properly, or if the first chamber fails to completely empty as required.

In the preferred method of the present invention, the first end of the first tube 102 is attached to a drain (not shown) that has been inserted into the appropriate subarachnoid region of the body. The appropriate valves associated with the proximal opening 106 of the first collection chamber 108 are opened and the appropriate valves associated with the distal end 112 of the collection chamber 108 are closed. In embodiments using four valves such as those shown in FIG. 3, the first and third valves 110 and 140 are opened and the second and fourth valves 116 and 142 are closed. The timer is also set for either a default or an alternate timer period and the maximum volume for the first chamber is also selected.

Thereafter, the fluid drains through the proximal valve(s) into the first collection chamber 108 through the use of gravity. As the fluid drains into the first chamber 108, the volume of the first chamber is constantly measured by the measuring device. Once the microprocessor determines that the first chamber 108 is filled to a preselected volume at any time prior to the expiration of the then applicable preselected time period, it will cause the proximal valve(s) to close and the distal valve(s) to open such that the first chamber will be emptied and the drainage will discontinue for the remainder of the preselected time period. In this manner, the drainage rate of the fluid will never be more than the preselected level during the preselected period of time. At the end of each preselected time period the timer will reset.

If the first chamber has not attained the maximum preselected volume in the preselected time period, the proximal valve(s) will remain open and the distal valve(s) will remain closed and the drainage will continue until the maximum volume is attained.

If at any time there is any problem with the system or if the first collection chamber fails to fully empty at each predetermined interval, an alarm will notify the appropriate personnel that their attention is required.

In addition, in the embodiments shown in FIGS. 1 and 2, the housing has an on/off button 160.

Further, in the preferred embodiments, the tubing, bags, collection chamber and first and second valves are all disposable and replaceable.

Those skilled in the art will understand that this type of apparatus is designed for use with CSF but it can be used in any other application in which the drainage amount of fluids over time is critical.

The embodiments and methods described above are exemplary embodiments and methods of the present invention. Those skilled in the art may now make numerous uses of, and departures from, the above-described embodiments and methods without departing from the inventive concepts disclosed herein. Thus, the construction of the embodiments and the steps of the methods disclosed herein are not limitations of the invention. Accordingly, the present invention is to be defined solely by the scope of the following claims.

What is claimed is:

1. An automated body fluid drain control apparatus, comprising:
    a collection chamber of a predetermined size;
    a first controllable flow means having an open and a closed state and a second controllable flow means having an open and a closed state, wherein the first controllable flow means is normally open and the second controllable flow means is normally closed so that body fluids collect in the chamber;
    a measuring device that automatically controls the amount of fluid entering the collection chamber through the first controllable flow means as a function of time;
    wherein when a predetermined amount of fluid is collected by the collection chamber before a first predetermined period of time elapses, the first controllable flow means is closed and the collection chamber ceases to collect the fluid.

2. The apparatus of claim 1, wherein when the first controllable flow means is closed and the collection chamber ceases to collect the fluid, the second controllable flow means is opened and the fluid is drained out of the collection chamber.

3. The apparatus of claim 2, further comprising an output device, wherein when the predetermined amount of fluid is collected by the collection chamber, the collection chamber releases the fluid into the output device.

4. The apparatus of claim 1 further comprising an alarm system for notifying when the apparatus is not operating properly.

5. The apparatus of claim 3 wherein after the first predetermined period of time has elapsed, the first controllable flow means is set to the open state and the second controllable flow means is set to the closed state, so that body fluids are again collected in the chamber, wherein when a predetermined amount of fluid is collected by the collection chamber before a second predetermined period of time elapses, the first controllable flow means is closed and the collection chamber ceases to collect the fluid.

6. The apparatus of claim 5 further comprising a third controllable flow means having an open and a closed state and positioned such that collected fluid passes the third controllable flow means before the first controllable flow means, wherein the third controllable flow means is normally open.

7. The apparatus of claim 6 further comprising a fourth controllable flow means having an open and a closed state and positioned such that collected fluid passes the fourth controllable flow means after the second controllable flow means, wherein the fourth controllable flow means is normally closed.

8. An apparatus for controlling the collection of body fluids, the apparatus comprising:
    a collection chamber,
    a first valve having an open and a closed state, wherein the first valve is normally open and allows body fluids to flow into the collection chamber,
    a second valve having an open and a closed state, wherein the second valve is normally closed so that body fluids collect in the chamber,
    a measuring device that measures the amount of fluid entering the collection chamber through the first valve during a predetermined first period of time,
    wherein if during the first period of time a predetermined volume of body fluid enters the chamber, the first valve is closed and the second valve is opened,
    wherein after the first period of time, the first valve is opened and the second valve is closed and a second period of time starts, wherein the first period of time is equal to the second period of time.

9. The apparatus of claim 8 further comprising a second collection chamber, wherein the second collection chamber collects fluids that drain from the first collection chamber after the second valve is opened.

10. The apparatus of claim 8 wherein if the first period of time has elapsed and the predetermined volume of fluid has not been collected, then the first valve remains open and the second controllable flow means remains closed until the predetermined volume has been collected, at which time the first valve closes and the second valve opens to drain the fluid from the collection chamber and the second period of time commences.

11. The apparatus of claim 10 further comprising a third valve having an open and a closed state and positioned such that collected body fluid passes the third valve before the first valve, wherein the third valve is normally open.

12. The apparatus of claim 11 further comprising a fourth control valve having an open and a closed state and positioned such that collected body fluid passes the fourth valve after the second valve, wherein the fourth valve is normally closed.

13. The apparatus of claim 8 wherein the first valve is positioned above the second valve and the apparatus is adapted to collect body fluids that drain via gravity.

14. The apparatus of claim 8 wherein the body fluid is cerebrospinal fluid.

15. An apparatus for controlling the collection of body fluids, the apparatus comprising:
    a collection chamber,
    a first valve in communication with the collection chamber, the first valve having an open and a closed state, wherein the first valve is normally open and allows body fluids to flow into the collection chamber,
    a second valve in communication with the collection chamber having an open and a closed state, wherein the second valve is normally closed so that body fluids collect in the chamber,
    a measuring device that measures the amount of fluid entering the collection chamber through the first valve as a function of time, and
    a controller that automatically controls the first and second valves,
        wherein the controller opens the second valve and closes the first valve if
            a) a first amount of fluid enters the collection chamber, or
            b) a first predetermined period of time elapses,
        wherein the controller opens the first valve and closes the second valve after the first period of time has elapsed, and a second period of time starts,
        wherein during the second period of time the controller opens the second valve and closes the first valve if
            a) the first amount of fluid enters the collection chamber, or
            b) the second period of time elapses,
        wherein the first period of time is equal to the second period of time.

16. The apparatus of claim 15 wherein the collection chamber has only one inlet.

17. The apparatus of claim 15 wherein the controller comprises a microprocessor.

18. The apparatus of claim 15 wherein in operation at least one of the first or second valves is closed.

19. The apparatus of claim 15 wherein the collection chamber defines an axis and the first and second valves are disposed along the axis.

20. The apparatus of claim 19 further comprising a second collection chamber, wherein the first valve is in fluid communication with the source of the body fluids and the second valve is in fluid communication with the second collection chamber.

* * * * *